(12) United States Patent
Boga et al.

(10) Patent No.: US 7,582,485 B2
(45) Date of Patent: *Sep. 1, 2009

(54) METHOD AND DEVICE FOR DETECTING AMMONIA ODORS AND HELICOBACTER PYLORI UREASE INFECTION

(75) Inventors: RameshBabu Boga, Roswell, GA (US); John Gavin MacDonald, Decatur, GA (US)

(73) Assignee: Kimberly-Clark Worldride, Inc., Neenah, WI (US)

( * ) Notice: Subject to any disclaimer, the term of this patent is extended or adjusted under 35 U.S.C. 154(b) by 58 days.

This patent is subject to a terminal disclaimer.

(21) Appl. No.: 10/687,327

(22) Filed: Oct. 16, 2003

(65) Prior Publication Data

US 2005/0084977 A1    Apr. 21, 2005

(51) Int. Cl.
*G01N 33/53*   (2006.01)
*G01N 33/00*   (2006.01)

(52) U.S. Cl. .................... 436/113; 435/7.1; 435/12; 422/61; 600/532

(58) Field of Classification Search .................. None
See application file for complete search history.

(56) References Cited

U.S. PATENT DOCUMENTS

| | | | |
|---|---|---|---|
| 2,015,864 A | | 10/1935 | Müller et al. |
| 2,429,694 A | * | 10/1947 | King ..................... 436/39 |
| 2,534,229 A | * | 12/1950 | Carhart et. al. ......... 436/109 |
| 2,593,146 A | | 4/1952 | Howard |
| 3,033,655 A | * | 5/1962 | Grosskopf ............... 422/86 |
| 3,193,404 A | * | 7/1965 | Davis .................... 427/288 |
| 3,266,973 A | | 8/1966 | Crowley |
| 3,338,992 A | | 8/1967 | Kinney |
| 3,341,394 A | | 9/1967 | Kinney |
| 3,381,688 A | | 5/1968 | Satas |
| 3,494,821 A | | 2/1970 | Evans |
| 3,502,538 A | | 3/1970 | Petersen |
| 3,502,763 A | | 3/1970 | Hartmann |

(Continued)

FOREIGN PATENT DOCUMENTS

EP            0103214           3/1984

(Continued)

OTHER PUBLICATIONS

Hart, Courtenay et al, Electrophoresis, vol. 24, pp. 588-598, 2003.*

(Continued)

*Primary Examiner*—Robert B Mondesi
*Assistant Examiner*—Ginny Portner
(74) *Attorney, Agent, or Firm*—Dority & Manning, P.A.

(57) ABSTRACT

The invention provides a breath testing device which visually indicates the presence of ammonia in a patient's breath, in particular ammonia from *helicobacter pylori* urease infection. The breath testing device comprises a visual indicating agent which changes color in response to ammonia odors, such as 4,4'-bis(dimethylamino)-benzhydrol (Michler's hydrol or BDMB), pararosaniline base and alpha-naphtholbenzein. The indicating agent is applied to a substrate which is then inserted into a tube or straw, which can be attached to the inlet of a breath collection balloon. When the patient blows into the tube or straw, the indicating agent will change color if it detects levels of ammonia which are consistent with *helicobacter pylori* urease infection.

16 Claims, 5 Drawing Sheets

U.S. PATENT DOCUMENTS

| | | | |
|---|---|---|---|
| 3,507,269 A | 4/1970 | Berry | |
| 3,542,615 A | 11/1970 | Dobo et al. | |
| 3,615,478 A | 10/1971 | Hoshino et al. | |
| 3,692,618 A | 9/1972 | Dorschner et al. | |
| 3,794,497 A | 2/1974 | Pratt et al. | |
| 3,802,817 A | 4/1974 | Matsuki et al. | |
| 3,836,633 A | 9/1974 | Bescke | |
| 3,842,103 A * | 10/1974 | Smith | 552/106 |
| 3,849,241 A | 11/1974 | Butin et al. | |
| 3,919,437 A | 11/1975 | Brown et al. | |
| 3,960,494 A | 6/1976 | Verma et al. | |
| 3,971,665 A | 7/1976 | Suzuki et al. | |
| 4,006,030 A | 2/1977 | Yoshida et al. | |
| 4,038,101 A * | 7/1977 | Thompson | 106/468 |
| 4,041,203 A | 8/1977 | Brock et al. | |
| 4,078,029 A | 3/1978 | Yoshida et al. | |
| 4,100,324 A | 7/1978 | Anderson et al. | |
| 4,101,638 A | 7/1978 | Inoue et al. | |
| 4,144,370 A | 3/1979 | Boulton | |
| 4,172,781 A | 10/1979 | Walk et al. | |
| 4,243,743 A * | 1/1981 | Hiramoto et al. | 430/281.1 |
| 4,297,233 A | 10/1981 | Gualandi | |
| RE30,797 E | 11/1981 | Davis | |
| RE30,803 E | 11/1981 | Davis | |
| 4,313,820 A | 2/1982 | Farha, Jr. et al. | |
| 4,340,563 A | 7/1982 | Appel et al. | |
| 4,375,448 A | 3/1983 | Appel et al. | |
| 4,407,960 A * | 10/1983 | Tratnyek | 436/1 |
| 4,467,012 A | 8/1984 | Pedersen et al. | |
| 4,469,746 A | 9/1984 | Weisman et al. | |
| 4,488,969 A | 12/1984 | Hou | |
| 4,494,278 A | 1/1985 | Kroyer et al. | |
| 4,494,629 A | 1/1985 | Raeburn | |
| 4,517,308 A | 5/1985 | Ehlenz et al. | |
| 4,522,203 A | 6/1985 | Mays | |
| 4,525,410 A | 6/1985 | Hagiwara et al. | |
| 4,548,906 A * | 10/1985 | Sekikawa et al. | 436/113 |
| 4,575,556 A | 3/1986 | Byrne et al. | |
| 4,604,313 A | 8/1986 | McFarland et al. | |
| 4,640,810 A | 2/1987 | Laursen et al. | |
| 4,643,801 A | 2/1987 | Johnson | |
| 4,655,757 A | 4/1987 | McFarland et al. | |
| 4,670,385 A * | 6/1987 | Babb et al. | 435/28 |
| 4,701,218 A | 10/1987 | Barker et al. | |
| 4,715,983 A | 12/1987 | Ota et al. | |
| 4,725,415 A | 2/1988 | Kidd | |
| 4,734,324 A | 3/1988 | Hill | |
| RE32,649 E | 4/1988 | Brandt et al. | |
| 4,769,216 A * | 9/1988 | Chandler et al. | 422/58 |
| 4,775,585 A | 10/1988 | Hagiwara et al. | |
| 4,777,018 A * | 10/1988 | Auchincloss | 422/28 |
| 4,780,448 A | 10/1988 | Broecker et al. | |
| 4,781,858 A | 11/1988 | Mizukami et al. | |
| 4,783,220 A | 11/1988 | Gamble et al. | |
| 4,798,603 A | 1/1989 | Meyer et al. | |
| 4,802,473 A | 2/1989 | Hubbard et al. | |
| 4,804,630 A * | 2/1989 | Bhattacharjee | 436/74 |
| 4,818,464 A | 4/1989 | Lau | |
| 4,823,404 A | 4/1989 | Morell et al. | |
| 4,823,803 A | 4/1989 | Nakamura | |
| 4,844,867 A * | 7/1989 | Bather | 422/60 |
| 4,853,186 A * | 8/1989 | Mura et al. | 422/55 |
| 4,854,332 A * | 8/1989 | Hanakura | 131/365 |
| 4,904,304 A | 2/1990 | Watanabe et al. | |
| 4,947,861 A * | 8/1990 | Hamilton | 600/532 |
| 4,969,457 A | 11/1990 | Hubbard et al. | |
| 4,978,615 A | 12/1990 | Aoyama et al. | |
| 4,988,505 A | 1/1991 | Watanabe et al. | |
| 5,000,746 A | 3/1991 | Meiss | |
| 5,020,533 A | 6/1991 | Hubbard et al. | |
| 5,057,302 A | 10/1991 | Johnson et al. | |
| 5,064,473 A | 11/1991 | Kubo et al. | |
| 5,094,962 A * | 3/1992 | Snyder et al. | 436/518 |
| 5,100,581 A | 3/1992 | Watanabe et al. | |
| 5,100,702 A | 3/1992 | Maeda et al. | |
| 5,108,739 A | 4/1992 | Kurihara et al. | |
| 5,122,418 A | 6/1992 | Nakane et al. | |
| 5,133,803 A | 7/1992 | Moffatt | |
| 5,145,518 A | 9/1992 | Winnik et al. | |
| 5,145,727 A | 9/1992 | Potts et al. | |
| 5,169,706 A | 12/1992 | Collier, IV et al. | |
| 5,174,959 A * | 12/1992 | Kundu et al. | 422/59 |
| 5,178,931 A | 1/1993 | Perkins et al. | |
| 5,183,656 A | 2/1993 | Uesaka et al. | |
| 5,188,885 A | 2/1993 | Timmons et al. | |
| 5,196,177 A | 3/1993 | Watanabe et al. | |
| 5,204,429 A | 4/1993 | Kaminsky et al. | |
| 5,209,998 A | 5/1993 | Kavassalis et al. | |
| 5,220,000 A | 6/1993 | Theodoropulos | |
| 5,221,497 A | 6/1993 | Watanabe et al. | |
| 5,225,374 A | 7/1993 | Fare et al. | |
| 5,230,953 A | 7/1993 | Tsugeno et al. | |
| 5,238,518 A | 8/1993 | Okubi et al. | |
| 5,245,117 A | 9/1993 | Withers et al. | |
| 5,266,289 A | 11/1993 | Tsugeno et al. | |
| 5,284,703 A | 2/1994 | Everhart et al. | |
| 5,286,624 A * | 2/1994 | Terashima et al. | 435/12 |
| 5,292,868 A | 3/1994 | Subramanian | |
| 5,294,717 A | 3/1994 | Theodoropulos | |
| 5,300,365 A | 4/1994 | Ogale | |
| 5,322,061 A | 6/1994 | Brunson | |
| 5,332,432 A | 7/1994 | Okubi et al. | |
| 5,338,713 A | 8/1994 | Takagi et al. | |
| 5,342,876 A | 8/1994 | Abe et al. | |
| 5,350,624 A | 9/1994 | Georger et al. | |
| 5,366,947 A | 11/1994 | Müller et al. | |
| 5,382,400 A | 1/1995 | Pike et al. | |
| 5,383,450 A | 1/1995 | Hubbard et al. | |
| 5,397,667 A | 3/1995 | Law et al. | |
| 5,407,442 A | 4/1995 | Karapasha | |
| 5,407,600 A | 4/1995 | Ando et al. | |
| 5,420,016 A * | 5/1995 | Boguslaski et al. | 435/12 |
| 5,420,090 A | 5/1995 | Spencer et al. | |
| 5,427,844 A | 6/1995 | Murai et al. | |
| 5,429,628 A | 7/1995 | Trinh et al. | |
| 5,432,094 A * | 7/1995 | Delente | 436/127 |
| 5,451,450 A | 9/1995 | Erderly et al. | |
| 5,458,864 A | 10/1995 | Tsugeno et al. | |
| 5,472,775 A | 12/1995 | Obijeski et al. | |
| 5,480,636 A | 1/1996 | Maruo et al. | |
| 5,486,356 A | 1/1996 | Yim | |
| 5,487,938 A | 1/1996 | Spencer et al. | |
| 5,488,126 A | 1/1996 | Subramanian et al. | |
| 5,527,171 A | 6/1996 | Soerensen | |
| 5,529,879 A * | 6/1996 | Hoshino et al. | 430/160 |
| 5,538,548 A | 7/1996 | Yamazaki | |
| 5,539,124 A | 7/1996 | Etherton et al. | |
| 5,540,916 A | 7/1996 | Parks | |
| 5,547,607 A | 8/1996 | Ando et al. | |
| 5,553,608 A | 9/1996 | Reese et al. | |
| 5,554,775 A | 9/1996 | Krishnamurti et al. | |
| 5,580,655 A | 12/1996 | El-Shall et al. | |
| 5,583,219 A | 12/1996 | Subramanian et al. | |
| 5,591,797 A | 1/1997 | Barthel et al. | |
| 5,597,512 A | 1/1997 | Watanabe et al. | |
| 5,661,198 A | 8/1997 | Inatani et al. | |
| 5,663,224 A | 9/1997 | Emmons et al. | |
| 5,679,138 A | 10/1997 | Bishop et al. | |
| 5,679,724 A | 10/1997 | Sacripante et al. | |
| 5,695,868 A | 12/1997 | McCormack | |
| 5,733,272 A | 3/1998 | Brunner et al. | |
| 5,773,227 A | 6/1998 | Kuhn et al. | |
| 5,795,985 A | 8/1998 | Hüsler et al. | |
| 5,813,398 A | 9/1998 | Baird et al. | |

| | | | |
|---|---|---|---|
| 5,814,370 A * | 9/1998 | Martino et al. ......... 427/213.35 |
| 5,817,300 A | 10/1998 | Cook et al. |
| 5,833,952 A * | 11/1998 | Grigor et al. ................ 424/49 |
| 5,837,352 A | 11/1998 | English et al. |
| 5,843,509 A | 12/1998 | Calvo Salve et al. |
| 5,855,788 A | 1/1999 | Everhart et al. |
| 5,861,144 A | 1/1999 | Peterson et al. |
| 5,871,872 A | 2/1999 | Matijevic et al. |
| 5,874,067 A | 2/1999 | Lucas et al. |
| 5,880,176 A | 3/1999 | Kamoto et al. |
| 5,880,309 A | 3/1999 | Suzuki et al. |
| 5,882,638 A | 3/1999 | Dodd et al. |
| 5,885,599 A | 3/1999 | Peterson et al. |
| 5,897,541 A | 4/1999 | Uitenbroek et al. |
| 5,902,226 A | 5/1999 | Tasaki et al. |
| 5,905,101 A | 5/1999 | Fujiki et al. |
| 5,916,596 A | 6/1999 | Desai et al. |
| 5,948,398 A | 9/1999 | Hanamoto et al. |
| 5,948,483 A | 9/1999 | Kim et al. |
| 5,962,566 A | 10/1999 | Grandfils et al. |
| 5,964,926 A | 10/1999 | Cohen |
| 5,972,389 A | 10/1999 | Shell et al. |
| 5,985,229 A | 11/1999 | Yamada et al. |
| 5,989,510 A | 11/1999 | Abe et al. |
| 5,989,515 A | 11/1999 | Watanabe et al. |
| 5,989,840 A * | 11/1999 | D'Angelo et al. .......... 435/7.32 |
| 6,004,625 A | 12/1999 | Ohshima |
| 6,007,592 A | 12/1999 | Kasai et al. |
| 6,024,786 A | 2/2000 | Gore |
| 6,039,923 A * | 3/2000 | Klemm et al. ................ 422/61 |
| 6,045,900 A | 4/2000 | Haffner et al. |
| 6,047,413 A | 4/2000 | Welchel et al. |
| 6,057,162 A | 5/2000 | Rounbehler et al. |
| 6,060,410 A | 5/2000 | Gillberg-LaForce et al. |
| 6,073,771 A | 6/2000 | Pressley et al. |
| 6,075,179 A | 6/2000 | McCormack et al. |
| 6,096,299 A | 8/2000 | Guarracino et al. |
| 6,111,163 A | 8/2000 | McCormack et al. |
| 6,171,811 B1 * | 1/2001 | Becerro De Bengoa Vallejo ........ 435/34 |
| 6,172,173 B1 | 1/2001 | Spencer et al. |
| 6,177,608 B1 | 1/2001 | Weinstrauch |
| 6,190,814 B1 | 2/2001 | Law et al. |
| 6,193,844 B1 | 2/2001 | McLaughlin et al. |
| 6,225,524 B1 | 5/2001 | Guarracino et al. |
| 6,228,605 B1 * | 5/2001 | Marshall .................... 435/34 |
| 6,238,767 B1 | 5/2001 | McCormack et al. |
| 6,254,894 B1 | 7/2001 | Denkewicz, Jr. et al. |
| 6,264,615 B1 | 7/2001 | Diamond et al. |
| 6,277,346 B1 | 8/2001 | Murasawa et al. |
| 6,277,772 B1 | 8/2001 | Gancet et al. |
| 6,291,535 B1 | 9/2001 | Watanabe et al. |
| 6,294,222 B1 | 9/2001 | Cohen et al. |
| 6,299,867 B1 | 10/2001 | Aoyagi et al. |
| 6,309,736 B1 | 10/2001 | McCormack et al. |
| 6,312,918 B1 * | 11/2001 | Ito et al. .................... 435/34 |
| 6,315,864 B2 | 11/2001 | Anderson et al. |
| 6,334,988 B1 | 1/2002 | Gallis et al. |
| 6,344,218 B1 | 2/2002 | Dodd et al. |
| 6,344,272 B1 | 2/2002 | Oldenburg et al. |
| 6,358,537 B1 | 3/2002 | Hoshino et al. |
| 6,358,909 B1 | 3/2002 | Ochomogo et al. |
| 6,369,290 B1 | 4/2002 | Glaug et al. |
| 6,376,741 B1 | 4/2002 | Guarracino et al. |
| 6,387,495 B1 | 5/2002 | Reeves et al. |
| 6,391,262 B1 * | 5/2002 | Brinton et al. ................ 422/61 |
| 6,398,827 B1 | 6/2002 | Ota et al. |
| 6,406,669 B1 * | 6/2002 | Duan et al. .............. 422/82.09 |
| 6,410,765 B1 | 6/2002 | Wellinghoff et al. |
| 6,416,729 B1 * | 7/2002 | DeBerry et al. .......... 423/573.1 |
| 6,425,530 B1 | 7/2002 | Coakley |
| 6,427,693 B1 | 8/2002 | Blackstock et al. |
| 6,428,814 B1 | 8/2002 | Bosch et al. |
| 6,433,243 B1 | 8/2002 | Woltman et al. |
| 6,440,187 B1 | 8/2002 | Kasai et al. |
| 6,460,989 B1 | 10/2002 | Yano et al. |
| 6,461,735 B1 | 10/2002 | Furuya et al. |
| 6,467,897 B1 | 10/2002 | Wu et al. |
| 6,468,500 B1 | 10/2002 | Sakaguchi et al. |
| 6,475,601 B1 | 11/2002 | Sakaki et al. |
| 6,479,150 B1 | 11/2002 | Liu et al. |
| 6,479,278 B2 * | 11/2002 | Marshall .................. 435/287.9 |
| 6,491,790 B1 | 12/2002 | Proverb et al. |
| 6,498,000 B2 | 12/2002 | Murasawa et al. |
| 6,509,169 B2 * | 1/2003 | Ratcliffe et al. ................ 435/34 |
| 6,517,199 B1 | 2/2003 | Tomioka et al. |
| 6,531,704 B2 | 3/2003 | Yadav et al. |
| 6,533,826 B1 * | 3/2003 | Gessner et al. ................. 8/634 |
| 6,536,890 B1 | 3/2003 | Kato et al. |
| 6,544,492 B1 * | 4/2003 | DeBerry ................. 423/573.1 |
| 6,548,264 B1 | 4/2003 | Tan et al. |
| 6,551,457 B2 | 4/2003 | Westman et al. |
| 6,562,441 B1 | 5/2003 | Maeda et al. |
| 6,575,383 B2 | 6/2003 | Dobler et al. |
| 6,578,521 B2 | 6/2003 | Raymond et al. |
| 6,589,562 B1 | 7/2003 | Shefer et al. |
| 6,589,761 B1 * | 7/2003 | Freadman et al. ............. 435/29 |
| 6,607,711 B2 | 8/2003 | Pedersen |
| 6,617,488 B1 * | 9/2003 | Springer et al. ............. 604/361 |
| 6,623,848 B2 | 9/2003 | Brehm et al. |
| 6,627,377 B1 * | 9/2003 | Itatani et al. ............. 430/270.1 |
| 6,638,918 B2 | 10/2003 | Davison et al. |
| 6,639,004 B2 | 10/2003 | Falat et al. |
| 6,645,569 B2 | 11/2003 | Cramer et al. |
| 6,693,071 B2 | 2/2004 | Ghosh et al. |
| 6,706,537 B2 * | 3/2004 | Ignacio et al. ............. 436/167 |
| 6,825,040 B2 * | 11/2004 | Scaringe et al. ............. 436/39 |
| 6,846,956 B2 * | 1/2005 | Kast et al. .................... 564/321 |
| 6,998,250 B2 * | 2/2006 | McMichael et al. ........... 435/34 |
| 7,014,612 B2 * | 3/2006 | Hubbard et al. ............. 600/532 |
| 7,022,285 B2 * | 4/2006 | Arai et al. .................... 422/56 |
| 7,052,854 B2 * | 5/2006 | Melker et al. ................ 435/7.1 |
| 7,101,340 B1 * | 9/2006 | Braun ....................... 600/532 |
| 7,316,899 B2 * | 1/2008 | McDevitt et al. ............... 435/6 |
| 7,413,550 B2 * | 8/2008 | MacDonald et al. ........ 600/532 |
| 2001/0000889 A1 | 5/2001 | Yadav et al. |
| 2001/0023338 A1 | 9/2001 | Guarracino et al. |
| 2001/0031248 A1 | 10/2001 | Hall-Puzio et al. |
| 2001/0056246 A1 | 12/2001 | Rodriguez-Fernandez et al. |
| 2002/0005145 A1 | 1/2002 | Sherman |
| 2002/0066542 A1 | 6/2002 | Jakob et al. |
| 2002/0068364 A1 * | 6/2002 | Arai et al. .................... 436/113 |
| 2002/0091071 A1 | 7/2002 | Fischer et al. |
| 2002/0106466 A1 | 8/2002 | Hausmann et al. |
| 2002/0110686 A1 | 8/2002 | Dugan |
| 2002/0128336 A1 | 9/2002 | Kolb et al. |
| 2002/0142937 A1 | 10/2002 | Carter et al. |
| 2002/0149656 A1 | 10/2002 | Nohr et al. |
| 2002/0150678 A1 | 10/2002 | Cramer et al. |
| 2002/0176982 A1 | 11/2002 | Rohrbaugh et al. |
| 2002/0177621 A1 | 11/2002 | Hanada |
| 2002/0182102 A1 | 12/2002 | Fontenot et al. |
| 2002/0182658 A1 * | 12/2002 | Polak et al. .................. 435/7.92 |
| 2003/0003589 A1 * | 1/2003 | Khalil et al. ................ 436/113 |
| 2003/0013369 A1 | 1/2003 | Soane et al. |
| 2003/0021744 A1 * | 1/2003 | DeBerry et al. ............. 423/228 |
| 2003/0021983 A1 | 1/2003 | Nohr et al. |
| 2003/0050211 A1 | 3/2003 | Hage et al. |
| 2003/0056648 A1 | 3/2003 | Fornai et al. |
| 2003/0070782 A1 | 4/2003 | Proverb et al. |
| 2003/0082237 A1 * | 5/2003 | Cha et al. .................... 424/490 |
| 2003/0100842 A1 | 5/2003 | Rosenberg et al. |
| 2003/0130631 A1 | 7/2003 | Springer et al. |
| 2003/0147956 A1 | 8/2003 | Shefer et al. |
| 2003/0147966 A1 | 8/2003 | Franzen et al. |
| 2003/0181540 A1 | 9/2003 | Quellet et al. |

| | | | |
|---|---|---|---|
| 2003/0203009 A1 | 10/2003 | MacDonald | |
| 2003/0203495 A1* | 10/2003 | Rupp | 436/74 |
| 2003/0211618 A1* | 11/2003 | Patel | 436/38 |
| 2003/0216660 A1* | 11/2003 | Ben-Oren et al. | 600/532 |
| 2003/0235605 A1 | 12/2003 | Lelah et al. | |
| 2004/0033269 A1 | 2/2004 | Hei et al. | |
| 2004/0034157 A1 | 2/2004 | Ghosh et al. | |
| 2004/0043688 A1 | 3/2004 | Soerens et al. | |
| 2004/0077093 A1* | 4/2004 | Pan | 436/37 |
| 2004/0122387 A1 | 6/2004 | Long et al. | |
| 2004/0175556 A1 | 9/2004 | Clark et al. | |
| 2004/0265742 A1* | 12/2004 | Marck et al. | 430/281.1 |
| 2005/0012085 A1* | 1/2005 | Lavi et al. | 256/65.14 |
| 2005/0037374 A1* | 2/2005 | Melker et al. | 435/6 |
| 2005/0084977 A1* | 4/2005 | Boga et al. | 436/113 |
| 2005/0085739 A1* | 4/2005 | MacDonald et al. | 600/530 |
| 2005/0112085 A1* | 5/2005 | MacDonald et al. | 424/76.1 |
| 2005/0124072 A1* | 6/2005 | Boga et al. | 436/111 |
| 2005/0164320 A1* | 7/2005 | McDevitt et al. | 435/7.92 |
| 2005/0186109 A1* | 8/2005 | Nakamura et al. | 422/56 |
| 2005/0191704 A1* | 9/2005 | Boga et al. | 435/7.1 |
| 2006/0003336 A1* | 1/2006 | Song et al. | 435/6 |
| 2007/0249958 A1* | 10/2007 | Martin et al. | 600/551 |
| 2008/0243015 A1* | 10/2008 | MacDonald et al. | 600/530 |

FOREIGN PATENT DOCUMENTS

| | | |
|---|---|---|
| EP | 0232141 | 8/1987 |
| EP | 0251783 | 1/1988 |
| EP | 0339461 | 11/1989 |
| EP | 0348978 A2 | 1/1990 |
| EP | 0376448 | 7/1990 |
| EP | 0389015 | 9/1990 |
| EP | 0389023 | 9/1990 |
| EP | 0483500 A1 | 5/1992 |
| EP | 0510619 A1 | 10/1992 |
| EP | 0282287 | 4/1996 |
| EP | 0972563 | 1/2000 |
| EP | 0749295 | 7/2000 |
| EP | 1034800 A1 | 9/2000 |
| EP | 001037045 A2 * | 9/2000 |
| EP | 1053788 | 11/2000 |
| EP | 1157672 | 11/2001 |
| EP | 1157672 A1 | 11/2001 |
| EP | 001160569 A2 * | 12/2001 |
| EP | 1162172 A1 | 12/2001 |
| EP | 1188854 A1 | 3/2002 |
| EP | 1214878 A1 | 6/2002 |
| EP | 1216675 A1 | 6/2002 |
| EP | 1298071 | 4/2003 |
| EP | 1315526 B1 | 6/2003 |
| JP | 62149322 | 7/1987 |
| JP | 3221142 | 9/1991 |
| JP | 92067913 * | 10/1992 |
| WO | WO 8902698 A1 | 4/1989 |
| WO | WO 9111977 A1 | 8/1991 |
| WO | WO 9112029 A1 | 8/1991 |
| WO | WO 9112030 A1 | 8/1991 |
| WO | WO 9619346 A2 | 6/1996 |
| WO | WO 9619346 A3 | 6/1996 |
| WO | WO 9705482 A1 | 2/1997 |
| WO | WO 9725076 A1 | 7/1997 |
| WO | 97/30351 * | 8/1997 |
| WO | WO 98/20915 | 5/1998 |
| WO | WO 9820915 A1 | 5/1998 |
| WO | WO 98/26808 | 6/1998 |
| WO | WO 9826808 A2 | 6/1998 |
| WO | WO 9826808 A3 | 6/1998 |
| WO | WO 99/47252 | 9/1999 |
| WO | WO 00/03797 | 1/2000 |
| WO | WO 0029036 A2 | 3/2000 |
| WO | WO 0029036 A3 | 3/2000 |
| WO | WO 00137764 A1 | 3/2000 |
| WO | 00/20852 * | 4/2000 |
| WO | WO 0059555 A1 | 10/2000 |
| WO | WO 00/76558 | 12/2000 |
| WO | WO 007658 A1 | 12/2000 |
| WO | WO 01/06054 | 1/2001 |
| WO | WO 02/26272 | 4/2002 |
| WO | WO 02/49559 | 6/2002 |
| WO | WO 02/55115 | 7/2002 |
| WO | WO 02/062881 | 8/2002 |
| WO | WO 02/064877 | 8/2002 |
| WO | WO 02/083297 | 10/2002 |
| WO | WO 02/084017 | 10/2002 |
| WO | WO 02/095112 | 11/2002 |
| WO | WO 02094329 A1 | 11/2002 |
| WO | WO 03/000979 | 1/2003 |
| WO | WO 03/025067 | 3/2003 |
| WO | WO 03032959 A1 | 4/2003 |
| WO | WO 03088931 A2 | 10/2003 |
| WO | WO 03/092885 | 11/2003 |
| WO | WO 2004000986 A1 | 12/2003 |

OTHER PUBLICATIONS

Rottman, Claudio et al, J. Am. Chem. Soc., vol. 123, pp. 5730-5734, 2001, Getting a library of activities from a single compound: Tunability and very large shifts in acidiity constants induced by sol-gel entrapped micells.*
Dunn, CDR et al, British Journal of Biomedical Science, vol. 58, pp. 66-75, 2001, Ammonia vapor in the mouth as a diagnostic marker for Helicobacter pylori infection: preliminary 'proof of principle' pharmacological investigations.*
Kearney, David J. et al, Digestive Disorders and Sciences, vol. 47(11) Nov. 2002, pp. 2523-2530, Breath Ammonia Measurement in Helicobacter pylori infection.*
Article—*Immunization of mice with peptomers covalently couopled to aluminum oxide nanoparticles*, Andreas Frey, Nicholas Mantis, Pamela A. Kozlowski, Alison J. Quayle, Adriana Bajardi, Juana J. Perdomo, Frank A. Robey, and Marian R. Neutra, Vaccine, vol. 17, 1999, pp. 3007-3019.
PCT Search Report for PCT/US03/39737, Jun. 18, 2004.
Abstract of Japanese Patent No. JPO4255767, Sep. 10, 1992.
Abstract of Japanese Patent No. JP05098185, Apr. 20, 1993.
Abstract of Japanese Patent No. JP57135360, Aug. 20, 1982.
Abstract of Japanese Patent No. JP2001208753, Mar. 8, 2001.
Abstract of Japanese Patent No. JP198610366, Jan. 11, 1986.
Article—*A sorbent tube for oral malodour monitoring*, Julia Rodriguez-Fernández, Regina López-Fernández, Rosario Pereiro, Manuel Menéndez, JoséMaría Tejerina, Alberto Sicilia, and Alfredo Sanz-Medel, Talanta, vol. 62, 2004, pp. 421-426.
Article—*Optical fibre sensor for hydrogen sulphide monitoring in mouth air*, Julio Rodríguez-Fernández, Rosario Pereiro, and Alfredo Sanz-Medel, Analytica Chimica Acta, vol. 471, 2002, pp. 13-23.
U.S. Appl. No. 10/723,761, filed Nov. 26, 2004, Quincy, III, et al. Odor Control In Personal Care Products.
U.S. Appl. No. 10/955,316, filed Sep. 30, 2004, MacDonald, et al. Odor-Reducing Quinone Compounds.
Abstract of Japanese Patent No. JP1262868, Oct. 19, 1989.
Abstract of Japanese Patent No. JP2157039, Jun. 15, 1990.
Abstract of Japanese Patent No. JP3195562, Aug. 27, 1991.
Abstract of Japanese Patent No. JP4335141, Nov. 24, 1992.
Abstract of Japanese Patent No. JP5261246, Oct. 12, 1993.
Abstract of Japanese Patent No. JP6285140, Oct. 11, 1994.
Abstract of Japanese Patent No. JP63072337, Apr. 2, 1988.
Abstract of Japanese Patent No. JP8152409, Jun. 11, 1996.
Abstract of SU834073, May 30, 1981.
PCT Search Report and Written Opinion for PCT/US2004/011596, Aug. 30, 2004.
PCT Search Report and Written Opinion for PCT/US2004/016933, Nov. 2, 2004.
Article—*Comparison of Non-Invasive Tests to Detect* Helicobacter Pylori *Infection in Children and Adolescents: Results of a Multicenter European Study*, Francis Mégraud, The Journal of Pediatrics, vol. 145, No. 2, Feb. 2005, pp. 198-203.

Article—*Increase of acetone and ammonia in urine headspace and breath during ovulation quantified using selected ion flow tube mass spectrometry*, Diskin et al., Physiological Measurement, vol. 24, Jan. 20, 2003, pp. 191-199.

Article—*Adsorption of Dyes on Nanosize Modified Silica Particles*, Guangwei Wu, Athanasia Koliadima, Yie-Shein Her, and Egon Matijevic, Journal of Colloid and Interface Sciences, vol. 195, 1997, pp. 222- 228.

Article—*Adsorption of Proteins and Antibiotics on Porous Alumina Membranes*, Yi Hua Ma, Aseem Bansal, and William M. Clark, Fundamentals of Adsorption, vol. 80, 1992, pp. 389-396.

Product Information Sheet for Snowtex®, 6 pages.

Article—*Significance of Ammonia in the Genesis of Gastric Epithelial Lesions Induced by Helicobacter pylori: An in vitro Study with Different Bacterial Strains and Urea Concentrations*, P. Sommi, V. Ricci, R. Fiocca, M. Romano, K.J. Ivey, E. Cova, E. Solcia, and U. Ventura, Digestion, vol. 57, 1996, pp. 299-304.

Article—*Ammonia vapour in the mouth as a diagnostic marker for Helicobacter pylori infection: preliminary "proof of principle" pharmacological investigations*, C. D. R. Dunn, M. Black, D. C. Cowell, C. Penault, N. M. Ratcliffe, R. Spence, and C. Teare, British Journal of Biomedical Science, vol. 58, 2001, pp. 66-76.

Article—*Purification and Characterization of Urease from Helicobacter pylori*, Bruce E. Dunn, Gail P. Campbell, Guillermo I. Perez- Perez, and Martin J. Blaser, The Journal of Biological Chemistry, vol. 265, No. 16, Jun. 5, 1990, pp. 9464-1990.

Article—*Validation of $^{13}$ C-Urea Breath Test for the Diagnosis of Helicobacter Pylori Infection in the Singapore Population*, T. S. Chua, K. M. Fock, E. K. Teo, T. M. Ng, Singapore Medical Journal, vol. 43, No. 8, 2002, pp. 408-411.

Article—*Significance of ammonia produced by Helicobacter pylori*, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.

Article—*Spectrophotometric Assay of Thiols*, Peter C. Jocelyn, Methods in Enzymology, vol. 142, 1987, pp. 44-67.

Abstract of Japanese Patent No. 7256025, Oct. 9, 1995.

PCT Search Report for PCT/US03/32846, Jun. 7, 2004.

Derwent Abstract, JP 5106199A, Apr. 1993, Nakajima et al.

Derwent Abstract, JP 9143872A, Jun. 1997, Sogawa.

Brunauer, S. et al., "Adsorption of Gases in Multimolecular Layers", *Journal of American Chemical Society*, vol. 60, Feb. 1938, pp. 309-319.

Béné, A. et al., "Applicability of a SPME Method for the Rapid Determination of VOCs", *Chimia*, 56, No. 6, 2002, ISSN 0009-4293, pp. 289-291.

Malik, D.J. et al., "Characterisation of Novel Modified Active Carbons and Marine Algal Biomass for the Selective Adsorption of Lead", *Water Research*, 36, 2002, pp. 1527-1538.

Cost, F., *Pocket Guide to Digital Printing*, Delmar Publishers, Albany, NY, ISBN 0-8273-7592-1, pp. 144-145.

Noller, C.R., "Saponins and Sapogenins. VIII. Surface Films of Echinocystic Acid and Derivatives", *The Journal of the American Chemical Society*, vol. 60, 1938, 3 pages.

Antonietti, M., "Synthesis of porous Silica with help from cyclodextrin aggregates", Max-Planck-Institut for Kolloid-und, Germany, 1 page.

Maldotti, A. et al., "Immobilization of $(n-Bu_4N)_4W_{10}$ $O_{32}$ on Mesoporous MCM-41 and Amorphous Silicas for Photocatalytic Oxidation of Cycloalkanes with Molecular Oxygen", *Journal of Catalysis*, vol. 209, 2002, pp. 210-216.

Zhang, Q. et al., "Fe-MCM-41 for Selective Epoxidation of Styrene with Hydrogen Peroxide", *The Chemical Society of Japan*, Chemistry Letters 2001, pp. 946-947.

Melde, B.J. et al., "Mesoporous Sieves with Unified Hybrid Inorganic/Organic Frameworks", *Chem. Mater.*, vol. 11, No. 11, 1999, pp. 3302-3308.

Polarz, S. et al., "From Cyclodextrin Assemblies to Porous Materials by Silica Templating", *Angew. Chem. Int. Ed.*, vol. 40, No. 23, 2001, pp. 4417-4421.

Shi, D. et al., "Uniform Deposition of Ultrathin Polymer Films on the Surfaces of $Al_2O_3$ Nanoparticles by a Plasma Treatment", University of Cincinnati and University of Michigan, Jun. 2000, pp. 1-15.

Santra, S. et al., "Development of novel dye-doped silica nanoparticles for biomarker application", *Journal of Biomedical Optics*, vol. 6, No. 2, Apr. 2001, pp. 160-166.

Buchhammer, M. et al., "Nanoparticles based on polyelectrolyte complexes: effect of structure and net charge on the sorption capacility for solved organic molecules", *Colloid Polym. Sci.*, vol. 278, 2000, pp. 841-847.

Brunauer, S. et al., "Adsorption of Gases in Multimolecular Layers", *The Journal of the American Chemical Society*, vol. 60, Feb. 1938, pp. 309-319.

Schaber, P.M. et al., "Study of the urea thermal decomposition (pyrolsis) reaction and importance to cyanuric acid production", *American Laboratory*, Aug. 1999, pp. 13-21.

Bergna, H.E., Editor, "Silanol Groups, Siloxane Bridges, and Physically Adsorbed Water", The Colloid Chemistry of Silica, American Chemical Society $200_{th}$ National Meeting, Aug. 26-31, 1990, pp. 22-23 and pp. 52-59.

Schweigert, I.V. et al., "Structure and properties of silica nanoclusters at high temperatures", *The American Physical Society*, Physical Review B, vol. 65, No. 235410, pp. 1-9.

Biermann, C.J. et al., Grafting of Poly(ethylenimine) onto Mesylated Cellulose Acetate, Poly(methyl methacrylate) and Poly(vinyl chloride), *Carbohydrate Polymers*, vol. 12, 1990, pp. 323-327.

Yurieva, T.M. et al., Abstract of "Non-hydrothermal synthesis of copper-, zinc- and copper-zinc hydrosilicates", *Materials Research Innovations*, vol. 5, No. 1, Jun. 2001, 2 pages.

\* cited by examiner

METHOD AND DEVICE FOR DETECTING AMMONIA ODORS AND HELICOBACTER PYLORI UREASE INFECTION

BACKGROUND OF THE INVENTION

The present invention relates to a method and device for detecting ammonia odors and uses thereof, in particular for diagnosing *helicobacter pylori* urease infection.

It is estimated that almost 1 in 10 adults will develop a stomach ulcer at some time in their lives. The bacterium *Helicobacter pylori* (HP) is known to be the cause of most stomach ulcers and ulcers of the duodenum and, once detected, can be cured by treatment with antibiotics. *H. pylori* (HP) produces an active form of the urease enzyme, which hydrolyzes urea into ammonia and carbon dioxide. Since ammonia is the key component generated by urease-catalyzed hydrolysis of urea, it follows that the presence of this compound in a person's breath can be used to diagnose *helicobacter pylori* urease (HPU) infection.

However, there are not many systems to detect ammonia odors, and of those available, most require the use of expensive instrumentation and are complex in operation (and hence not suitable for use by untrained users).

In general, HPU infection is diagnosed by analyzing the difference of exhaled ammonia and/or $CO_2$ levels from a patient before and after swallowing a dose of radioactive urea. The levels of ammonia in HPU infected persons are usually between 100 to 200 parts per million (ppm) after swallowing the urea, whereas the levels of ammonia in an uninfected person after having swallowed the urea are much the same as before taking the urea (<2 ppm).

The patient first drinks a solution of citric acid as a background test and two baseline expired breath samples are collected in Mylar breath collection balloons from Kimberly-Clark/Ballard Medical Devices of Draper, Utah. The patient then drinks a second solution containing citric acid and carbon-14 labeled urea, and another two expired breath samples are taken after 30 minutes. The samples of expired breath are then analyzed for carbon-14 labeled carbon dioxide. The test is considered positive for *H. Pylori* infection when the difference between the control breath and the labeled breath samples are greater than 3.5 parts per thousand. This test is both expensive and time consuming.

Therefore, there is a clear need for a simple, safe device which needs neither expensive instrument nor radioactive materials for detecting ammonia from HPU infection and other sources.

SUMMARY OF THE INVENTION

This invention describes a simple device for detecting ammonia odors using a visual indicating agent which changes color when ammonia is present in the breath of a user, in particular when the ammonia is present in the range of 20 to 500 parts per million (ppm), more preferably in the range of 50 to 400 ppm, and most preferably in the range of 75 to 300 ppm.

The indicating agent is also suitable for diagnosing *helicobacter pylori* urease (HPU) infection, which causes ammonia to be present in a patient with the infection. The development of potential stomach ulcers can thus be inhibited or the stomach ulcers can be treated at an early stage.

The visual indicating agent is typically a dye which is color sensitive to ammonia odors, such as 4,4'-bis(dimethylamino)-benzhydrol (BDMB or Michler's hydrol (MH)), a dye having a similar chemical structure to MH, a triamino-triphenyl-methanol dye such as pararosaniline base (PAB), alpha-naphtholbenzein or any other dye which has high sensitivity for ammonia. The dye may change color by fading to a lighter color, by deepening in color or by actually changing from one color to another.

The device includes a simple carrier portion defining a passage, such as a substantially transparent tube or straw, containing the visual indicating agent. While the invention will be described hereinafter with particular reference to straws and tubes, it will be understood that the invention is useful with various other shapes as well. For example, the shape of the passageway may be cylindrical, triangular, square, almond-shaped and so forth.

The visual indicating agent may be in the form of a powder, in solution (for example, in water, an aqueous solution, toluene or alcohol), or may be coated onto a substrate, such as cellulose tissue or paper, a nonwoven fabric substrate, a woven substrate, glass fiber, cotton, silk, rayon and so forth. The solution may be applied to the substrate and dried so that a dry residue of the indicating agent remains on the substrate. The straw may be substantially flattened to allow for easier storage, while still permitting a patient to blow through the passage in the tube. The device may include a zone with one or more reference colors to allow the user to compare the color of the indicating agent after exposure to his or her breath with the reference color, and so easily determine if there has been a color change.

In one embodiment, the visual indicating agent is coated onto a cellulose substrate which is then inserted into a straw. In another embodiment, the visual indicating agent is again coated onto a cellulose susbstrate, but is placed over one end of a straw.

In both embodiments, when the patient blows into the tube, their breath will pass through the tube and over or through the substrate, thus causing the indicating agent to change color if levels of ammonia which are indicative of HPU infection (generally between 20 and 500 ppm) are present in the patient's breath.

The breath testing devices may be single-use devices which are disposable.

Thus, HPU infection can be detected by a simple color change, and there is no need for radioactive urea and complex instrumentation. No similar system has yet been developed or reported in the literature.

The straw may be connected to the inlet of a breath collection balloon such as the type sold commercially by Kimberly-Clark/Ballard Medical Devices of Draper, Utah for use in the existing *H. pylori* detection kits (PYtest™ 14C-Urea Breath Test). The use of such a balloon would help ensure that the correct amount of breath was sampled, as the patient would simply blow through the straw into the balloon until it was fully inflated.

The patient may ingest urea prior to his or her breath being tested so as to boost the ammonia levels which are detected. After a period of time sufficient to allow HPU, if present, to hydrolyze the urea into ammonia and carbon dioxide, the patient would then blow into a breath testing device. If the patient were infected with HPU, sufficient amounts of ammonia would be present in his or her breath to be detected by the device, and the indicating agent would show a change in color.

DETAILED DESCRIPTION OF THE INVENTION

The invention provides simple breath testing devices which are able to detect levels of ammonia odors in a patient's breath which are consistent with *helicobacter pylori* urease infection without requiring the patient to ingest radio-active chemicals. Thus, the breath testing devices include a visual indicating agent which changes color in response to the ammonia odors, preferably when the ammonia is in the range of 20 to 500 parts per million (ppm), more preferably in the range of 50 to 400 ppm, and most preferably in the range of 75 to 300 ppm.

In one embodiment, the visual indicating agent is 4,4'-bis(dimethylamino)-benzhydrol, also known as "BDMD", "Michler's hydrol" or "MH". This indicating agent is sensitive to both sulphur-containing and amine-containing odors, changing from blue to colorless in the presence of these odors. Michler's Hydrol reacts with amine or sulfur compounds according to the following reaction:

(Colorless)

Michler's Hydrol
(MH or BDMB)

(Blue Color)

(Colorless)

Michler—s hydrol (MH) and related indicating agents, which are also suitable for use as indicating agents for the present invention, can be represented by the following general formula (I) or (II):

| Indicating Agent | R | R' | R" | Indicating Agent for |
|---|---|---|---|---|
| Michler's Hydrol (MH) | $(CH_3)_2NC_6H_5-$ | $(CH_3)_2NC_6H_5-$ | H | Ammonia, Amines, Diamines and Polyamines |
| Pararosaniline Base (PAB) | $(NH_2)C_6H_5-$ | $(NH_2)C_6H_5-$ | $(NH_2)C_6H_5-$ | Ammonia, Amines, Diamines and Polyamines |

-continued $$R-\underset{R''}{\overset{OH}{\underset{|}{C}}}-R' \xrightarrow{H^+} R-\underset{R''}{C}=R' \quad \text{where,}$$
(I) (II)

| Indicating Agent | R | R' | R" | Indicating Agent for |
|---|---|---|---|---|
| Alpha-naphtholbenzein (ANB) | $C_6H_5-$ | (structure with HO-naphthyl=naphthyl=O) | | Ammonia, Amines, Diamines and Polyamines |
| Naphthochrome Green (NCG) | $C_6H_5-$ | $NaO_2C$ (structure with HO-naphthyl=naphthyl=O, $CO_2Na$) | | Ammonia, Amines, Diamines and Polyamines |

The dye may change color by fading to a lighter color, by deepening in color or by actually changing from one color to another. Thus, MH changes from blue to colorless, PAB changes from red to colorless and ANB changes from yellow/orange to grey in the presence of ammonia.

The degree of the color change will depend on the concentration of the indicating agent or the concentration of ammonia in the patient's breath. Therefore, in order to observe a color change in response to ammonia levels in the range of 75 to 300 ppm, the concentration of indicating agent which is used is preferably in the range of from 0.01 to 15% wt/wt, more preferably from 0.05 to 2% wt/wt, and most preferably from 0.1 to 0.5% wt/wt.

In one embodiment, the visual indicating agent is coated onto a cellulose substrate which is then inserted into a straw. In another embodiment, the visual indicating agent is again coated onto a cellulose susbstrate, but is placed over one end of a straw.

The substrate, typically a cellulose tissue, may also be coated with nanoparticles to provide a high surface area coating on the substrate, i.e., higher than the cellulose fiber by itself. Thus, the cellulose tissue may be given a boost in surface area by coating it with nanoparticles. The treated substrate may be then coated with the visual indicating dye. It's believed that this high surface area coating helps spread the dye over the silica surface to provide a thinner coating and thus improving the sensitivity of the device.

The average size of the nanoparticles is generally less than about 100 nanometers, in fact it may be from about 1 to about 50 nanometers, and from about 4 to about 20 nanometers. As used herein, the average size of a particle refers to its average length, width, height, and/or diameter.

The nanoparticles may have a surface area of from about 50 square meters per gram ($m^2/g$) to about 1000 $m^2/g$, in some cases from about 100 $m^2/g$ to about 600 $m^2/g$, and in some cases, from about 180 $m^2/g$ to about 240 $m^2/g$.

In addition, the nanoparticles may also be relatively non-porous or solid. That is, the nanoparticles may have a pore volume that is less than about 0.5 milliliters per gram (ml/g), less than about 0.4 ml/gram, less than about 0.3 ml/g, and even from about 0.2 ml/g to about 0.3 mug. It is believed that the solid nature, i.e., low pore volume, of the nanoparticles may enhance the uniformity and stability of the nanoparticles.

Examples of commercially available alumina nanoparticles include, for instance, Aluminasol® 100, Aluminasol® 200 and Aluminasol® 520, which are available from Nissan Chemical America Corporation of Houston, Tex., USA. Alternatively, silica nanoparticles may be utilized, such as Snowtex-C®, Snowtex-O®, Snowtex-PS® and Snowtex-OXS® nanoparticles, which are also available from Nissan Chemical.

Snowtex-OXS® nanoparticles, for instance, have a particle size of from 4 to 6 nanometers, and may be ground into a powder having a surface area of approximately 509 square meters per gram. Also, alumina-coated silica particles may be used, such as Snowtex-AK® nanoparticles available from Nissan Chemical.

The breath testing device includes a simple supporting member, such as a substantially transparent tube or straw containing the visual indicating agent. The visual indicating agent may be in the form of a powder, in solution, or may be coated onto a substrate, such as cellulose tissue or paper, cotton, a non-woven fabric substrate, a woven substrate, glass fiber, silk, rayon and so forth. The indicating agent may also be printed onto the substrate, for example by using an inkjet printer.

The straw or tube may be substantially flattened to allow for easier storage, while still permitting a patient to blow through the passage in the tube.

The device may include a zone with one or more reference colors or shades of color to allow the user to compare the color of the indicating agent after exposure to his or her breath with the reference color, and so easily determine if there has been a color change.

In both embodiments, when the patient blows into the tube, their breath will pass through the tube and over or through the substrate, thus causing the indicating agent to change color if levels of ammonia which are indicative of HPU infection (generally from 20 to 500 ppm, more particularly from 50 to 400 ppm and most particularly between 75 to 300 ppm) are present in the patient's breath.

The straw or tube may be connected to the inlet of a breath collection balloon such as the type sold commercially by Kimberly-Clark/Ballard Medical Devices of Draper, Utah for use in the existing *H. pylori* detection kits (PYtest™ 14C-Urea Breath Test). Such a test balloon has a volume of about 0.5 to 2 liters or about 1 lung-full of breath for most individuals. The use of such a balloon helps ensure that the correct amount of breath is sampled. If too much breath is sampled, the device may provide a false positive diagnosis, and if too little breath is sampled, the device may provide a false negative diagnosis. Thus, the patient would simply blow through the straw into the balloon until it was fully inflated.

According to another embodiment, the breath testing devices described above were made smaller in size so that several of the breath testing devices could be easily packaged together in a pocket-sized container. For example, a straw was cut to about 4 cm in length, and a dye-treated substrate was either inserted into the straw or was placed over one end of the straw. The straw was then substantially flattened by laminating it in a standard business card heated laminator so that air was still able to pass through the tube of the straw.

The patient may ingest urea prior to his or her breath being tested so as to boost the ammonia levels which are detected. After a period of time sufficient to allow HPU, if present, to hydrolyze the urea into ammonia and carbon dioxide, the patient would then blow into the breath testing device. If the patient were infected with HPU, sufficient amounts of ammonia would be present in his or her breath to be detected by the device, and the indicating agent would show a change in color.

Unless otherwise specified, chemicals and biochemicals were obtained from Sigma-Aldrich of Milwaukee, Wis.

The most widely used color test is called CIELAB and is discussed in *Pocket Guide to Digital Printing* by F. Cost, Delmar Publishers, Albany, N.Y. ISBN 0-8273-7592-1 at pages 144 and 145. This method defines three variables, L*, a*, and b*, that correspond to three characteristics of perceived color based on the opponent theory of color perception. The three variables have the following meaning:

L*=Lightness, ranging from 0 to 100. Where 0=dark and 100=light, a*=Red/green axis, ranging approximately from −100 to 100. Positive values are reddish and negative values are greenish.

b*=Yellow/blue axis, Ranging approximately from −100 to 100. Positive values are yellowish and negative values are blueish.

Because CIELAB color space is somewhat uniform, a single number can be calculated that represents the difference between two colors as perceived by a human being. This difference is termed ΔE and is calculated by taking the square root of the sum of the squares of the three differences (ΔL*, Δa*, and Δb*) between the two colors. In CIELAB color space, each ΔE unit is roughly a just-noticeable difference between two colors. So that the two colors have a difference of, for example, 4.4, the human eye can perceive the difference in color between the two colors. CIELAB is therefore a good measure for an objective device-independent color specification system that can be used as a reference color space for the purpose of color management and expression of changes in color.

Color intensities (L*a*b* values) herein were measured using a handheld spectrophotometer from Minolta Co. Ltd. of Osaka, Japan (Model # CM2600d). This instrument utilizes the D/8 geometry conforming to CIE No. 15, ISO 7724/1, ASTM E1164 and JIS Z8722-1982 (diffused illumination/8 degree viewing system. The D65 light reflected by the specimen surface at an angle of 8 degrees to the normal of the surface is received by the specimen-measuring optical system.

Absorbance readings were measured using a microplate reader from Dynex Technologies of Chantilly, Va. (Model # MRX).

An acetate buffer containing 40 mM sodium acetate and 4 M guanidine HCl, pH 5.1, was used for preparations of the indicating agents.

Paper towels or KIMWIPES® tissues from Kimberly-Clark Corporation of Neenah, Wis., were coated with Snowtex-O® nanoparticles (pH 4.1), available from Nissan Chemical and were used in the examples described herein with Michler's hydrol dye (MH or BDMB) or pararosaniline base (PAB), where dye was added without acetate buffer, unless otherwise indicated.

The invention will now be described in more detail by way of the following non-limiting examples.

EXAMPLE 1

Figure 1:
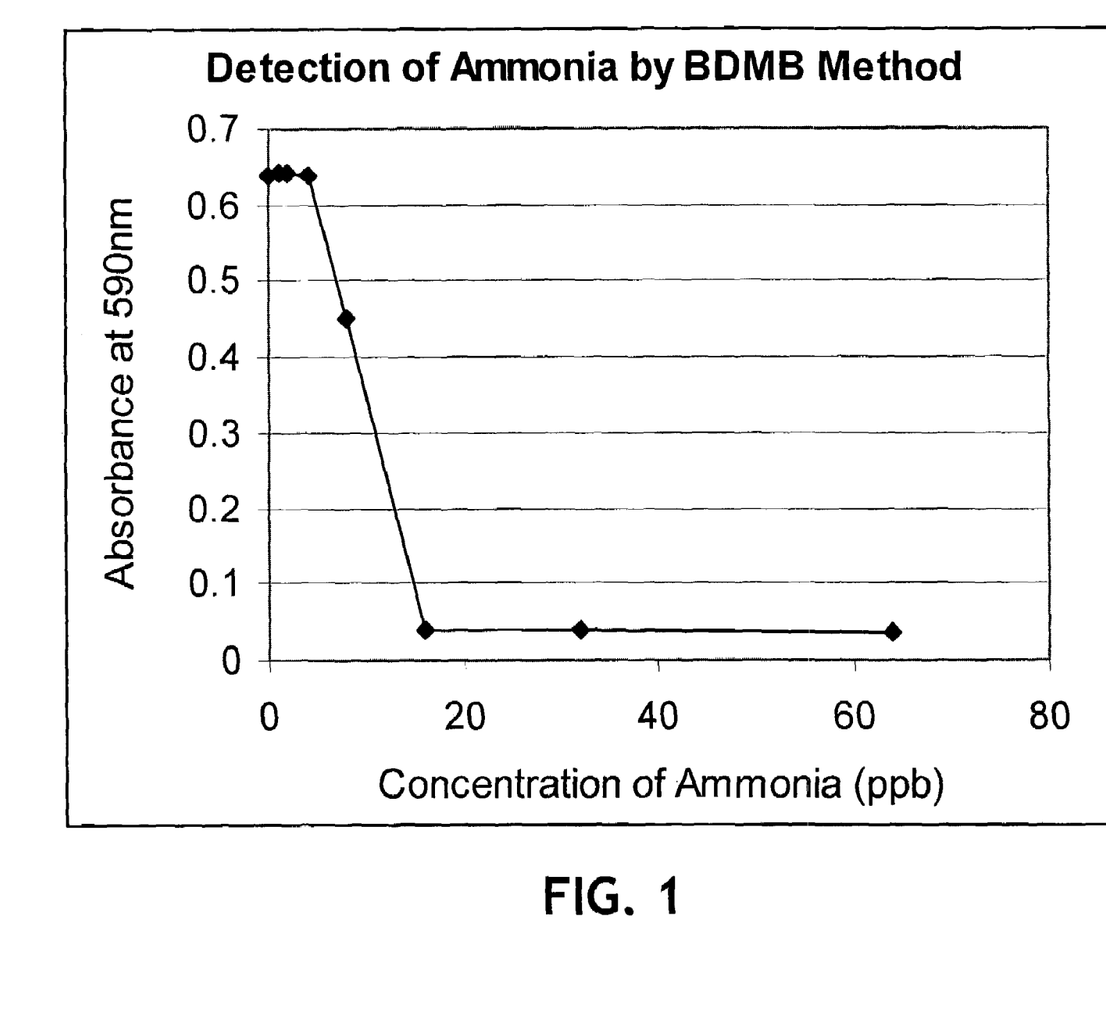
FIG. 1 shows a standard curve for the detection of ammonia by Michler's Hydrol-dye.

A reaction mixture was placed into each of 8 vials containing 50 μl of ammonia hydroxide solution as an ammonia source (0, 0.01, 0.02, 0.04, 0.08, 0.16 and 0.64% of ammonia hydroxide, respectively) and 150 μl of MH dye (20 μl of 10.0 mg/ml MH in $CH_3CN$ with 5.0 ml of 40 mM sodium acetate and 4M guanidine HCl, pH5.1). After incubation of all the vials at room temperature for less than 4 minutes, a 200 μl portion from each vial was transferred to a microtiter plate well, and the absorbances were measured at 590 nm using a microtiter plate reader (The absorbances can also be measured in the range of 580-615 nm).

As shown in FIG. 1, a standard curve was derived by plotting the absorbance readings against the concentrations (ppb) of ammonia solutions. In FIG. 1, the x-axis is the concentration of ammonia in parts per billion (ppb) from 10 to 400 and the y-axis is the absorbance at 590 nm from 1 to 0.7. The sensitivity of ammonia detection by MH was shown to be very high.

EXAMPLE 2

Figure 2:
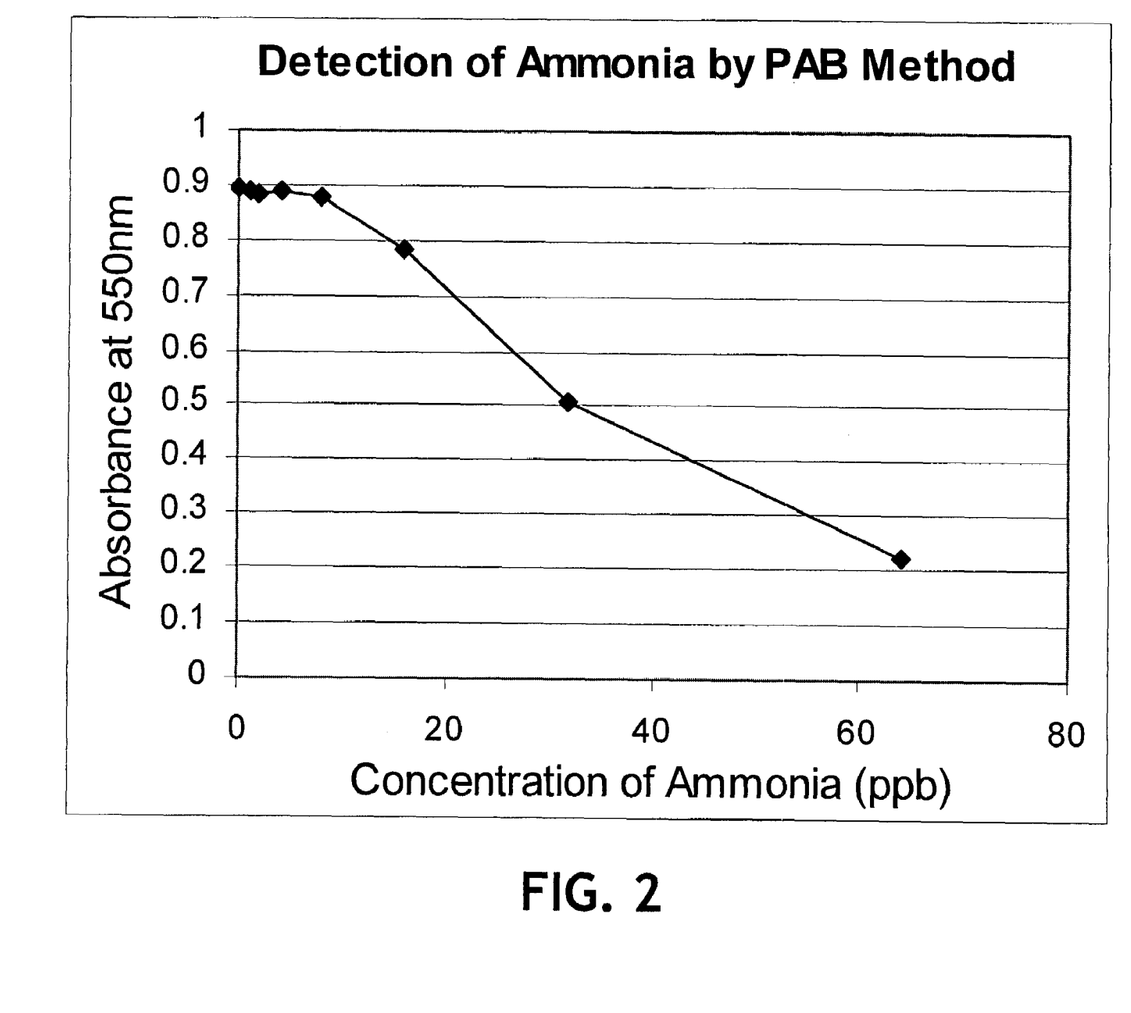
FIG. 2 shows a standard curve for the detection of ammonia by pararosaniline base (PAB)

A similar study was carried out with another dye, pararosaniline base (PAB), which was shown to be sensitive to amine and ammonia odors. In order to generate a standard curve (FIG. 2), a reaction mixture was placed into each of 8 vials containing 50 μl of an ammonia hydroxide solution as an ammonia source (0, 0.01, 0.02, 0.04, 0.08, 0.16 and 0.64% of ammonia hydroxide, respectively) and 150 μl of PAB solution (10 μl of 10 mg/ml PAB stock solution made in $CH_3CN$ with 5.0 ml of 40 mM sodium acetate and 4 M guanidine HCl, pH5.1). 200 μl of each reaction mixture was transferred to a mictotiter plate well and the wells were incubated at room temperature for 4 to 5 min. The absorbances were then read at 550 nm using a microplate reader. PAB was shown to be highly selective for ammonia and amine odors. In FIG. 2, the x-axis is the concentration of ammonia in parts per billion (ppb) from 10 to 400 and the y-axis is the absorbance at 550 nm from 1 to 1.0.

EXAMPLE 3

Figure 3:
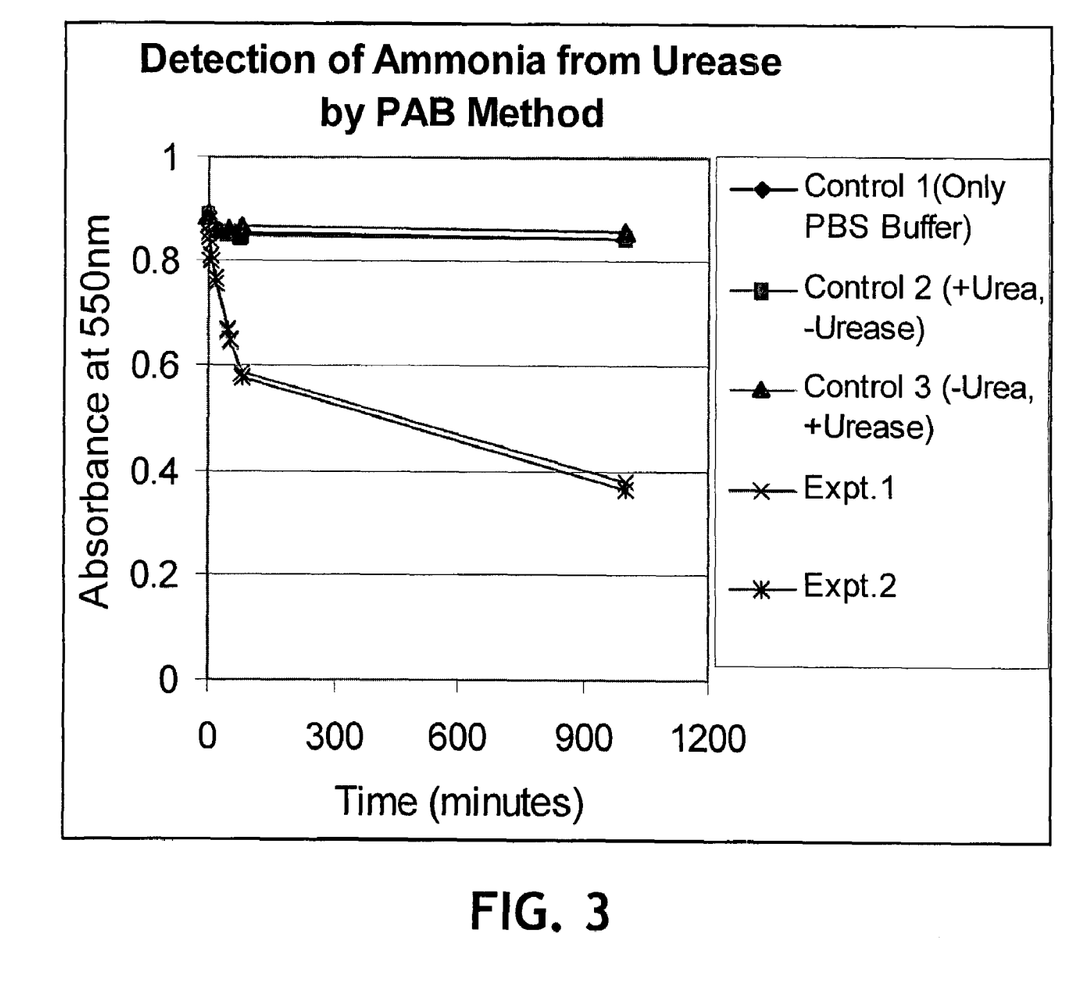
FIG. 3 shows the results of a test to monitor the hydrolysis of urea to ammonia and carbon dioxide using PAB.

PAB was then used to see if it was suitable for use in monitoring the reaction in which urease catalyzes urea to ammonia and carbon dioxide by-products (FIG. 3). Into each of two vials (expt. 1 and expt. 2) was placed 1 ml of a reaction mixture containing 100 µl of 10 mM urea, 850 µl of 10 mM PBS, pH7.3, and 50 µl of 10.0 mg/ml urease. Three control vials were prepared, the first control excluding both urea and urease (control 1), the second control excluding urease but containing urea (control 2), and the third control excluding urea but containing urease (control 3). The vials were vortexed and 50 µl from each vial was transferred to a microtiter plate well. PAB solution (10 µl of 10 mg/ml PAB stock solution made in $CH_3CN$ with 5.0 ml of 40 mM sodium acetate and 4 M guanidine HCl, pH5.1) was then added to each well and the absorbance change with time was monitored at 550 nm using a microplate reader. In FIG. 3, the x-axis is time in minutes and the y-axis is the absorbance at 590 nm from 1 to 1.0. As can be seen in FIG. 3, the three controls had relative constant absorbance over time while the two experimental samples had falling absorbance over time. The PAB did not show any interference with buffer, urea, or urease alone, and was shown to be sensitive for ammonia generated by the urease reaction with urea.

EXAMPLE 4

Figure 4:
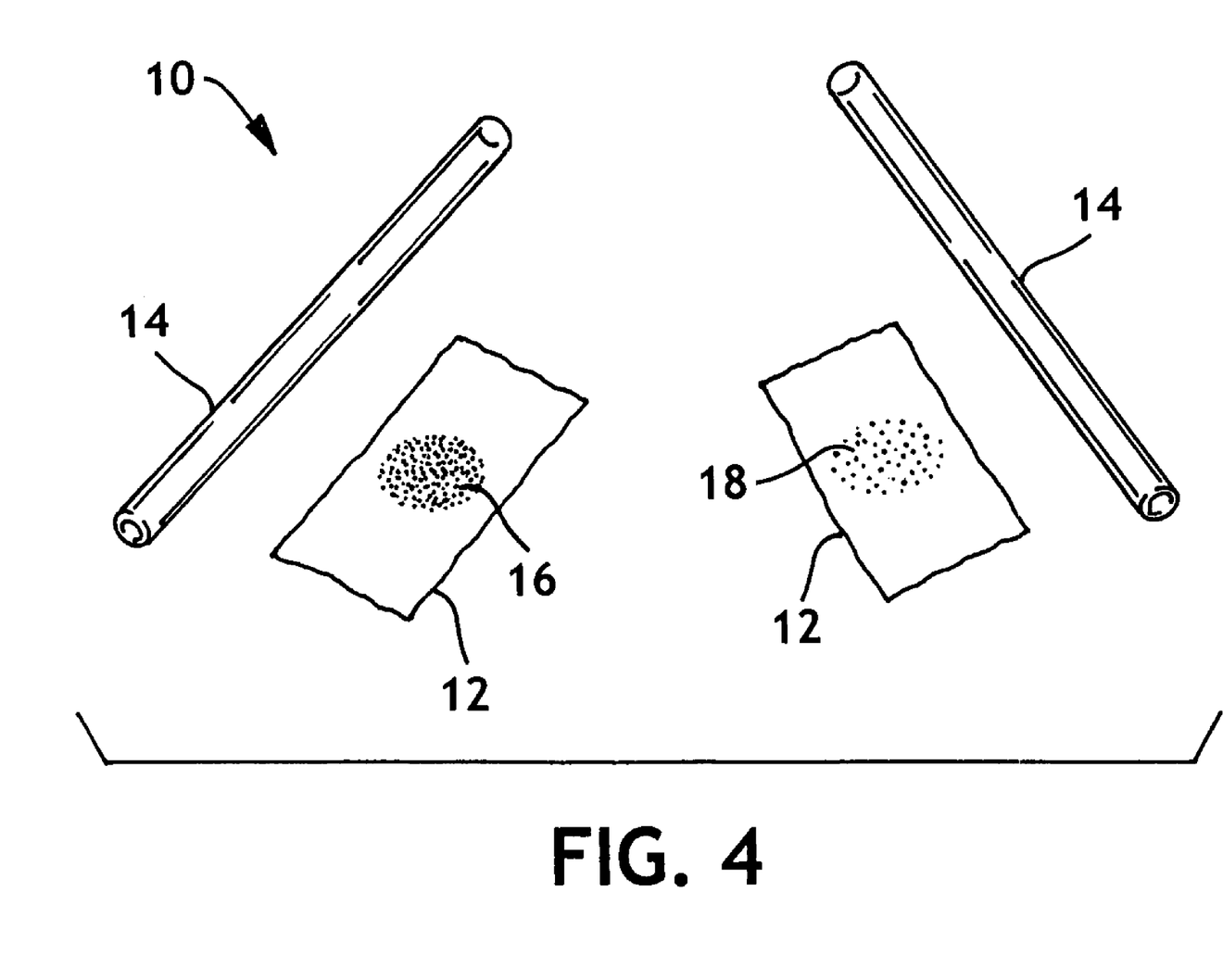
FIG. 4 shows simple breath testing device according to a first embodiment of the invention in an unassembled state, demonstrating a color change in the indicating agent before (left) and after (right) exposure to ammonia odors.

A first embodiment of a device 10 for detecting HPU infection was designed using an ammonia-odor sensitive dye coated on a cellulose substrate (FIG. 4). Accordingly, 1 mg/ml stock solution of MH-dye was applied onto a SCOTT® paper towel from Scott Paper of Mississauga, ON, Canada, that had been previously coated with a 1 weight percent (dry) solution of SNOWTEX-O® nanoparticles and allowed to air dry. The dye-coated paper towel was then cut into 2 cm×4 cm strips 12 which were rolled up and each strip 12 was inserted into a clear plastic drinking straw 14 from Glad Products Company of Oakland, Calif.

The devices were tested by injecting known concentrations of ammonia hydroxide into the straws to determine their sensitivity to ammonia odors. A color change (from blue 16 to colorless 18) was noticed and was clearly visible in the presence of ammonia odors.

The experiment was repeated using PAB-dye and alpha-naphtholbenzein dye instead of MH-dye. On exposure to ammonia odors, the dye-coated substrates were observed to change from red to colorless and from yellow/orange to grey, respectively.

The color intensities (La*b*) of the indicating dye showed a clear difference between before and after the exposure to ammonia odors (~100 ppb). The level of detection of ammonia odor by either MH or PAB (~100 ppb) is far less compared to the physiological level generated from urea hydrolysis by HP urease, $V_{max}$, 1,100±200 µmol of urea hydrolyzed/min/mg of protein.

Several volunteers who had already been diagnosed with HPU infection were also given a number of these straws and were asked to blow into them with one lung-full of breath. A color change of the indicating dye on the substrate within the tubes was easily observed with the unaided eye.

EXAMPLE 5

As an alternative to coating a solution of the indicating agent onto a cellulose substrate as described in example 4 above, a solution of the indicating agent was formulated into an inkjet printable ink. Inkjet printing deposits a thin coating of dye on top of the substrate, potentially allowing a more sensitive color coating on the substrate. The Michler's Hydrol dye solution was formulated with inkjet additives shown in Table 1 below.

TABLE 1

Inkjet formulation

| INK COMPONENT | VOLUME (ml) |
|---|---|
| Water (deionized) | 0.85 |
| Ethylene Glycol | 3.0 |
| Glycerol | 1.5 |
| Polyethylene Glycol (200 MW) | 3.0 |
| 1,3-Propanediol | 1.5 |
| Michler's Hydrol (1.5 mg/ml) in 40 mM sodium acetate and 4 M guanidine HCl, pH 5.1 | 40.1 |
| TOTAL | 50 |

The ink solution was loaded into empty Margarita® cartridges (part no. 0900400-300) obtained from McDermid-Colorspan of Eden Prairie, Minn. and printed using a wide format McDermid-Colorspan printer (Model XII). A strip of the printed Scott® paper towel was then exposed to ammonia odor and the blue color was observed to decolorize in about 10 seconds (compared to 3-5 minutes taken to observe the color change of a Scott® paper towel saturated with MH according to one of the previous examples). Higher sensitivity to the odor was thus observed by inkjet printing the indicating agent onto the substrate.

EXAMPLE 6

KIMWIPES® tissues were coated with a 5% Snowtex-O® nanoparticle solution from Nissan Chemical and then air-dried. 5.0 mg/ml stock solution of MH-dye in acetonitrile was applied to the Snowtex-O nanoparticle-coated KIMWIPES® tissues and a blue color was observed to develop as the applied dye solution dried.

Figure 5:
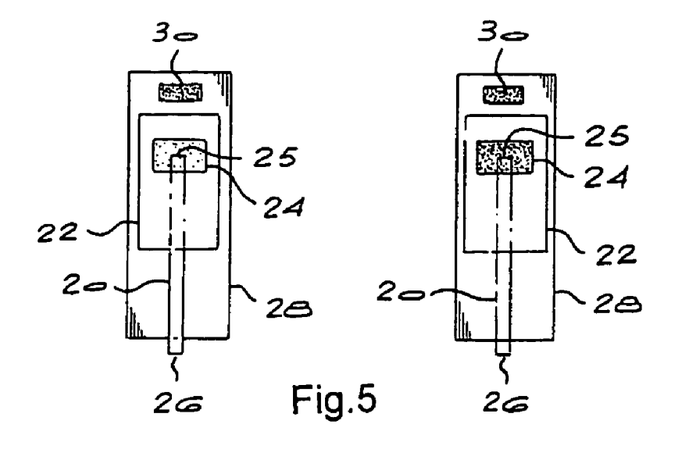
FIG. 5 shows a second embodiment of a breath testing device according to the invention with a color reference, before (right) and after (left) exposure to ammonia odors.

As shown in FIG. 5, a drinking straw 20 from Glad Products Company of Oakland, Calif., was placed on a cardboard strip 22, and a piece of the dye-nanoparticle coated tissue 24 was placed over a first end 25 of the straw. Thus, when a patient breathes into the second end 26 of the straw, their breath would pass through the tissue 24 at the first end of the straw. The straw was placed between two sheets of polyethylene 28 which were then heat-sealed so that only the second end 26 of the straw was exposed. A reference (or control) color strip 30 was also placed between the polyethylene sheets near, but separate from, the first end 25 of the straw and sealed when the polyethylene sheets were heat sealed. This reference strip consists of a piece of the dye-coated tissue and allows the patient to compare the color of the strip 24 at the end of the drinking straw with the reference strip 30 to see if there has been a color change (left), and hence to determine whether he or she has HPU infection. The reference strip could also consist of a scale of two or more shades of blue so that the user could compare the change of color of the tissue in the straw with the scale, and so determine the degree of infection. For example, a slight change in the color could represent mild infection, a more pronounced fade to a lighter blue could represent medium infection, and a complete change from blue to colorless could represent severe infection.

EXAMPLE 7

The devices described in examples 4 and 6 were reduced in size to make them more discreet and easy to carry around.

Figure 6:
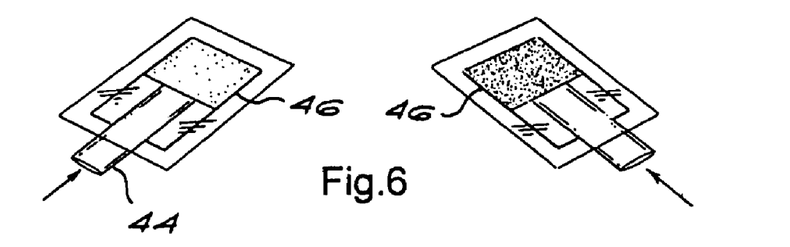
FIG. 6 shows a third embodiment of the breath testing device according to the invention.
Figure 7:
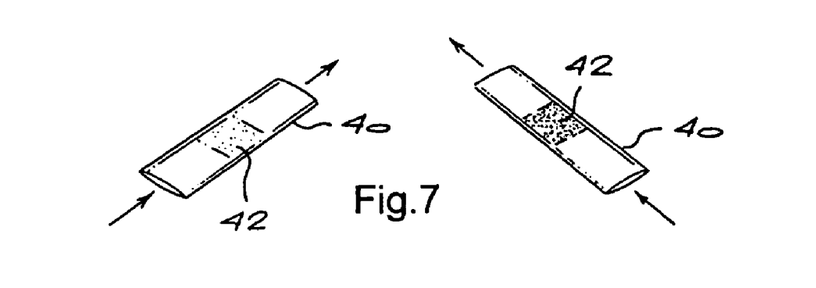
FIG. 7 shows a fourth embodiment of the breath testing device according to the invention.

Two minitiarized breath testing devices were therefore developed:

a) The first prototype (FIG. 7) was prepared by taking the article of example 4 (i.e. a drinking straw 40 into which a dye-treated tissue 42 had been inserted) and making the tube of the drinking straw shorter, for example, 4 cm long. The straw was then placed into a standard business card heated laminator (from Kinko's of Dallas, Tex.) so that the tube was flattened but air was still able to pass through the tube.

b) The second prototype (FIG. 6) was prepared by taking the article of example 6 (i.e. a drinking straw 44 having a dye-treated tissue strip 46 covering one end of the straw), and again cutting it to a length of approximately 4 cm. The straw was laminated as above.

EXAMPLE 8

Figure 8:
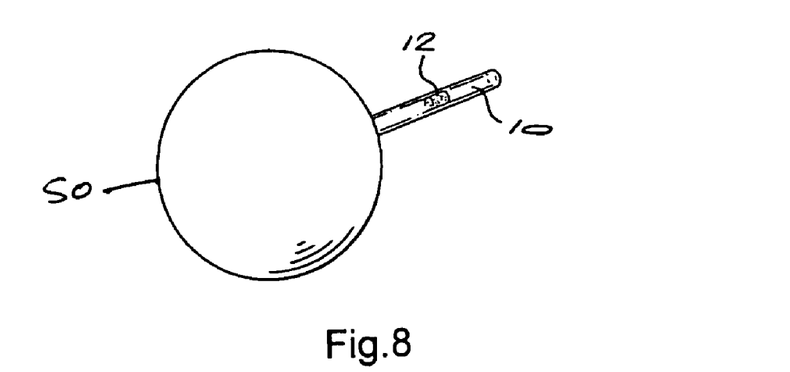
FIG. 8 shows the breath testing device of FIG. 4 in conjunction with a breath collection balloon.

In order to ensure that the HPU testing devices as described above would detect the levels of ammonia which are exhaled by patients having ulcers, it is preferable that a uniform amount of breath is sampled. Thus, the device described in example 4 was attached to a breath collection balloon 50 from Kimberly-Clark/Ballard Medical Devices of Draper, Utah (FIG. 8), discussed above. The patient would therefore blow through the device 10 into the balloon until the balloon becomes inflated, and if the substrate 12 with the indicating agent within the device 10 changed color after exposure to this amount of breath, this would indicate that the patient is suffering from HPU infection.

From the above examples, it can be seen that it is possible to detect HPU infection using a visual indicating agent which is sensitive to ammonia and/or amine odors, rather than requiring a patient to ingest radioactive materials and to use expensive and complex equipment.

While the invention has been described in detail with respect to specific embodiments thereof, it will be apparent to those skilled in the art that various alterations, modifications and other changes may be made to the invention without departing from the spirit and scope of the present invention. It is therefore intended that the claims cover or encompass all such modifications, alterations and/or changes.

What is claimed is:

1. A kit for detecting *Hellcobacter pylori*, the kit comprising a breath testing device that contains a substrate on which a visual indicating agent is disposed that is color sensitive to ammonia at a concentration of about 20 to about 500 parts per million, wherein the substrate is located within a tubular carrier portion of a breath collecting device through which the breath of a user passes, wherein the visual indicating agent contains Michler's hydrol, and wherein the substrate further comprises nanoparticles having an average size of less than about 100 nanometers.

2. The kit of claim 1, wherein the visual indicating agent is sensitive to ammonia at a concentration of about 50 to about 400 parts per million.

3. The kit of claim 1, wherein the breath testing device comprises a reference zone.

4. The kit of claim 1, wherein the nanoparticles have a surface area of from about 50 to about 1000 square meters per gram.

5. The kit of claim 1, wherein the nanoparticles include silica, alumina, or combinations thereof.

6. The kit of claim 1, wherein the substrate contains a fibrous material.

7. The kit of claim 6, wherein the fibrous material contains cellulosic fibers.

8. The kit of claim 1, wherein the carrier portion is open at least one end.

9. The kit of claim 8, wherein the carrier portion is substantially flattened.

10. The kit of claim 8, wherein the carrier portion is connected to a balloon.

11. The kit of claim 1, wherein the substrate covers an end of a carrier portion of the breath collecting device.

12. The kit of claim 1, wherein the visual indicating agent is applied to the substrate as a solution.

13. The kit of claim 12, wherein the concentration of the visual indicating agent is from about 0.001 to about 15% wt/wt of the solution.

14. The kit of claim 12, wherein the concentration of the visual indicating agent is from about 0.005 to about 2% wt/wt of the solution.

15. The kit of claim 1, further comprising a source of urea, the urea being hydrolyzable in the presence of a urease enzyme to generate ammonia.

16. The kit of claim 1, wherein the carrier portion is transparent.

* * * * *

UNITED STATES PATENT AND TRADEMARK OFFICE
CERTIFICATE OF CORRECTION

PATENT NO. : 7,582,485 B2  Page 1 of 1
APPLICATION NO. : 10/687327
DATED : September 1, 2009
INVENTOR(S) : Boga et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 323 days.

Signed and Sealed this

Fourteenth Day of September, 2010

David J. Kappos
*Director of the United States Patent and Trademark Office*